United States Patent [19]

Mendoza

[11] Patent Number: 4,740,636

[45] Date of Patent: Apr. 26, 1988

[54] DI-ORTHO-SUBSTITUTED DI-META-HALOGENATED PARA-HALOMETHYLPHENOLS

[75] Inventor: Abel Mendoza, Midland, Mich.

[73] Assignee: The Dow Chemical Company, Midland, Mich.

[21] Appl. No.: 49,918

[22] Filed: May 15, 1987

Related U.S. Application Data

[62] Division of Ser. No. 858,473, Apr. 30, 1986, Pat. No. 4,684,752.

[51] Int. Cl.[4] .............................................. C07C 39/24
[52] U.S. Cl. .................................... 568/774; 568/779
[58] Field of Search ............................. 568/774, 779

[56] References Cited

U.S. PATENT DOCUMENTS 4,328,361  5/1982  Dai ..................................... 568/774
4,684,752  9/1987  Mendoza ........................... 568/779

FOREIGN PATENT DOCUMENTS 0533584  6/1974  U.S.S.R. ............................. 568/779

*Primary Examiner*—Werren B. Lone

[57] ABSTRACT

Included is a process to prepare a 4-HALOmethyl-3,5-dihalo-2,6-disubstitutedphenol from a 4-methyl(substituted)phenol and a HALOgenating agent, in an aprotic organic diluent. The process is highly selective and efficient. For example, high purity 4-bromomethyl-3,5-dibromo-2,6-dimethylphenol can be prepared from 2,4,6-trimethylphenol and bromine, in bromochloromethane at high conversion.

5 Claims, No Drawings

DI-ORTHO-SUBSTITUTED DI-META-HALOGENATED PARA-HALOMETHYLPHENOLS

CROSS REFERENCE TO RELATED APPLICATION

This is a divisional of application Ser. No. 858,473, filed Apr. 30, 1986, now U.S. Pat. No. 4,684,752.

FIELD

This invention concerns halogenated phenols, with a process to prepare them. The halogenated phenols are useful flame retardants, fungicides and monomers.

BACKGROUND

"Halomethylation" of aromatics is a well established reaction. However, halomethylation of phenols is generally not a selective process. In general, it is difficult to obtain monomeric chloromethylated products. See, G. A. Olah, *Friedel-Crafts* and Related Reactions, Vol. II, Part 2, pp. 701–11, 1964. Halogenation of alkylphenols is normally accompanied by side-reactions. V. V. Ershov, A. A. Volodkin & G. N. Bogdanov, *Russion Chemical Reviews*, 32, 75–93 (1963). Furthermore, bromomethylation, in general, affords lower yields than chloromethylation, ibid., pp. 734–735.

The preparation of a halogenated phenol such as 4-bromomethyl-3,5-dibromo-2,6-dimethylphenol (tribromomesitol) can involve the following sequence: bromination of 2,4,6-trimethylphenol (mesitol) with 2 moles of bromine in acetic acid to prepare 3,5-dibromo-2,4,6-trimethylphenol (dibromometisol) which is isolated by precipitation with water. K. Auwers & F. Rapp, *Ann.*, 302, 153–71 (1898) and O. Jacobsen, *Ann.*, 195, 265–92 (1879); the dibromomesitol is brominated in acetic acid sodium acetate buffer at low temperatures to afford an intermediate, 3,4,5-tribromo-2,4,6-trimethyl-2,5-cyclohexadienone, which is isolated by fast precipitation with water and filtration; this solid slowly rearranges to tribromomesitol at room temperature, more quickly at higher temperatures. K. Fries & E. Brandes, *Ann.*, 542, 48–77 (1939). This procedure to prepare tribromomesitol is complex and not industrially viable.

A more direct method of preparation of tribromomesitol involves the reaction of mesitol in glacial acetic acid with an excess of bromine, using 10.6 moles of bromine per mole of mesitol. The yields are 66 percent and the product isolation is difficult. K. Auwers and H. Allendorff, *Ann.*, 302, 76–98 (1898). This procedure is not industrially viable either.

Chlorination of 3,5-dichloro-2,4,6-trimethylphenol in trifluoroacetic acid is known to produce 3,4,5-trichloro-2,4,6-trimethyl-2,5-cyclohexadienone or 3,5,6-trichloro-2,4,6-trimethyl-2,4-cyclohexadienone. Antinori et al., *J. Chem. Soc.* (*B*), 373–77 (1969).

SUMMARY

The invention is a process for preparing a 4-HALOmethyl-3,5-dihalo-2,6-disubstituted phenol comprising contacting a 4-methyl(substituted)phenol with a HALOgenating agent, in an aprotic organic diluent, under conditions whereby the 4-HALOmethyl-3,5-dihalo-2,6-disubstitutedphenol is prepared. The process is simple, highly selective and highly efficient. Characteristically, in general, the process requires no light nor the presence of base, and it can be run under moderate temperatures. The 4-HALOmethyl-3,5-dihalo-2,6-disubstitutedphenols are useful flame retardants, fungicides and monomer precursors for phenolic resins and engineering thermoplastics.

ILLUSTRATIVE EMBODIMENTS

Herein, the (exclusively upper case) syllabic "HALO" refers to a halogen selected from the group consisting of chlorine and bromine. "Halo" refers to any halogen, preferably selected from the group consisting of fluorine, chlorine and bromine. Thus, for example, a bromo moiety is both "HALO" and "halo"; whereas a fluoro moiety is only "halo".

The 4-HALOmethyl-3,5-dihalo-2,6-disubstitutedphenols are a type of halogenated phenol. The 4-HALOmethyl-3,5-dihalo-2,6-disubstitutedphenols include compounds of the general formula

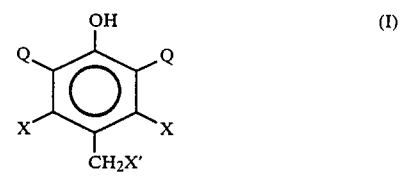

wherein

Q is separately at each occurrence alkyl (with at most secondary (2°) carbon bonded directly to the phenol ring) or generally inertly-substituted alkyl, each preferably maximally of about 12 carbons ($C_{1-12}$), more preferably the alkyl and most preferably methyl;

X is separately at each occurrence one of the halo moieties, more preferably HALO and most preferably Br; and X' is HALO and preferably Br.

The most preferred of the 4-HALOmethyl-3,5-dihalo-2,6-disubstitutedphenols is 4-bromomethyl-3,5-dibromo-2,6-dimethylphenol.

The 4-methyl(substituted)phenols include compounds of the general formula

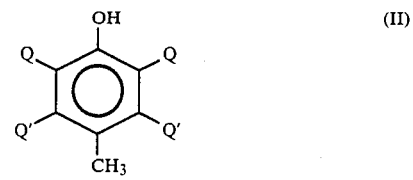

wherein

Q is as defined herein, and each Q generally corresponds to each Q of the compounds of the formula (I); and Q' is separately at each occurrence hydro (H) or X (as defined herein) and preferably H.

The most preferred of the 4-methyl(substituted)phenols is 2,4,6-trimethylphenol (mesitol).

The generally inertly-substituted alkyl (Q) moieties are those substituted alkyl moieties which do not, in general, interfere with the process for preparing the corresponding 4-HALOmethyl-3,5-dihalo-2,6-disubstitutedphenol. For example, the generally inertly-substituted alkyl moiety can be an alkyl moiety which is substituted with a moiety such as an ether moiety or a halo moiety.

The 4-methyl(substituted)phenols can be commercially obtained or prepared by known procedures or by the process herein, which can be employed to prepare the 4-methyl(substituted)phenols of the formula (II), for example, with the desired halo Q' moiety. The 4-methyl(substituted)phenols, for example, of the formula (II) with each Q' hydro, are commercially available (for example, 2,4,6-trimethylphenol) or they can be prepared by known procedures, for example, by the processes disclosed by U.S. Pat. Nos. 2,841,623 (1958), Norton et al.; Walts et al., 3,360,573 (1967); Van Sorge, 3,751,488 (1973) and 3,764,630 (1973); Suzuki et al., 3,899,540 (1975) and 3,976,702 (1976) (each incorporated herein by reference).

The HALOgenating agent is a means for imparting a HALO (Cl; Br) moiety to (at least the 4-methyl moiety of) the 4-methyl(substituted)phenol to prepare the 4-HALOmethyl-3,5-dihalo-2,6-disubstitutedphenol.

Thus, the HALOgenating agent is a suitable source of HALO moiety. The HALOgenating agent can include molecular HALOgens which include the elemental HALOgens, elemental bromine ($Br_2$) and elemental chlorine ($Cl_2$), and compounds such as, for example, bromine chloride. The HALOgenating agent can be an organic HALOgenating agent such as, for example, N-bromosuccinimide (a suitable source of the bromo moiety) and sulfuryl chloride (a suitable source of the chloro moiety).

Preferably, the HALOgenating agent is the molecular HALOgen. Preferably, the molecular HALOgen is elemental bromine.

The aprotic organic diluent is generally inert. Thus, the aprotic organic diluent does not, in general, interfere with the process to prepare the 4-HALOmethyl-3,5-dihalo-2,6-disubstitutedphenol. In general, the aprotic organic diluent is a liquid under the conditions of the process and preferably is a liquid at about room temperature (25° C.). The aprotic organic diluent is preferably considered generally such as a liquid solvent. The aprotic organic diluent can thus include diluents such as alkanes such as, for example, cyclohexane; haloalkanes such as, for example, dichlorofluoromethane, methylene chloride, chloroform, carbon tetrachloride, bromochloromethane, ethylene dichloride; and halogenated aromatics such as, for example, ortho-dichlorobenzene. However, the heterocyclic ether tetrahydrofuran, when employed as the sole aprotic organic diluent, typically does not enhance the higher efficiencies of the process, and it is thus not preferred.

Preferred of the aprotic organic diluents are the haloalkanes. Most preferably, the haloalkane is bromochloromethane.

In the practice of the invention, the 4-methyl(substituted)phenol is contacted with the HALOgenating agent. Conditions are those sufficient to prepare the 4-HALOmethyl-3,5-dihalo-2,6-disubstitutedphenol.

Amounts of the HALOgenating agent thus required can, in general, range from about one atomic equivalent to about ten atomic equivalents per mole of the 4-methyl(substituted)phenol reactant. The atomic equivalents are based on the equivalents of HALO moiety generally available from the HALOgenating agent for imparting to the 4-methyl(substituted)phenol to prepare the 4-HALOmethyl-3,5-dihalo-2,6-disubstitutedphenol. For example, one mole of the molecular HALOgen elemental bromine generally contains one atomic equivalent of bromo moiety available for the imparting to the 4-methyl(substituted)phenol. Typically, upon the HALOgenation, a by-product of hydrogen chloride or bromide is produced.

In general, the ratio of the atomic equivalents of the HALOgenating agent employed per mole of the 4-methyl(substituted)phenol (converted to any of the halogenated phenols) can be from about 1:1 to about 7:1, and with each Q' moiety halo, for example, to about 5:1. Preferably, with the Q' moiety of the 4-methyl(substituted)phenol each hydro, the ratio of the atomic equivalents of the halogenating agent employed per mole of the 4-methyl(substituted)phenol (converted to any of the halogenated phenols) is from about 3:1 to about 5:1 and most preferably from about 3.2:1 to about 4:1. Thus, it is most preferred that at least about one atomic equivalent of the HALOgenating agent or slightly more is employed per molar equivalent of the 4-methyl moiety of the 4-methyl(substituted)phenol.

A halogenating agent other than the HALOgenating agent may be employed to impart other halo moieties, for example, to the 3 or 5 positions of the ring with hydro for a Q' moiety. The other halogenating agent can thus be a fluorinating agent such as, for example, perchloryl fluoride ($ClO_3F$). The use of the HALOgenating agent is preferred.

Amounts of the aprotic organic diluent thus required can, in general, vary over a wide range. Preferably, the amount is sufficient to prepare a slurry or solution with the reactants or products. Preferably, the ratio of moles of aprotic organic diluent employed per mole of the 4-methyl(substituted)phenol is from about 5:1 to 1000:1 and more preferably from 10:1 to 50:1. The aprotic organic diluent can be used to initially dilute either the 4-methyl(substituted)phenol or halogenating agent, for example, the HALOgenating agent, or a plurality of them.

Temperatures employed can generally range from cool to elevated temperatures. The cool temperatures include temperatures such as about room temperature (25° C.) or below to temperatures such as to minus 120° C. and preferably to about 0° C. The elevated temperatures include temperatures of 30° C. or above, preferably to 100° C. and more preferably from about 35° C. to about 85° C.

For the most part, the cool temperatures are preferably employed in initial stages such as which can impart appropriate halo moieties to the 3 or 5 positions of the ring. Also, the cool temperatures are preferably employed throughout with the HALOgenating agent such as elemental chlorine (or even halogenating agent such as perchloryl fluoride). And, the elevated temperatures are preferably employed thereafter especially, for example, with the HALOgenating agent such as elemental bromine. In general, the higher the temperature is, the faster the rate of the process becomes.

Pressures employed can, in general, vary over a wide range. The pressure employed can be supra- or subatmospheric. However, ambient pressure is generally preferred during the preparation.

Time (duration) of the process can, in general, vary over a broad range, for example, from a few minutes to several days. Preferably, the time of carrying out the process is from about half an hour to about ten hours and more preferably from about one hour to about seven hours. Most preferably, the time employed is from about two to about five hours, especially with the HALOgenating agent such as elemental bromine because typically greater than about ninety percent of the 4-methyl(substituted)phenols are converted to the appropriate product within the span of this latter time period. Shorter times can typically be employed when employing more of the HALOgenating agent.

The 4-HALOmethyl-3,5-dihalo-2,6-disubstitutedphenols can often be employed as thus prepared, especially such as with, for example, from about 95 percent to 99 percent (by weight) purity, or can be further purified by known methods. Preferably, purification involves recrystallization such as, for example, from toluene, carbon tetrachloride, methylene chloride or bromochloromethane.

In general, the process is highly selective and efficient. Preferably, the conversion of the 4-methyl(substituted)phenol to any (more) halogenated phenol (converted product) is thus 50 percent (by weight) or greater, and can be about 65 percent or greater, even 80 percent or greater. Selectivity of the thus converted product to the 4-HALOmethyl-3,5-dihalo-2,6-disubstitutedphenol itself can thus be as high as 80 percent (by weight) of the converted product or above, even as high as 90 percent of the converted product or above, more preferably about 95 percent of the converted product or above. Selectivity of the isolated product as high as 98 percent (by weight) or above, including 99 percent, can be thus obtained even without recrystallization. Thus, the yield of the 4-HALOmethyl-3,5-dihalo-2,6-disubstitutedphenol (in general: decimal value of the conversion multiplied by decimal value of the selectivity, multiplied by 100 percent) can be high. Preferably, the yield is thus 40 percent (by weight) or above, more preferably 50 percent or above and can be about 65 percent or above. The yield of the 4-HALOmethyl-3,5-dihalo-2,6-disubstitutedphenol can thus even be as high as about 75 percent, even 80 percent, or above, by weight.

The following preferred sequence generally illustrates the overall process:

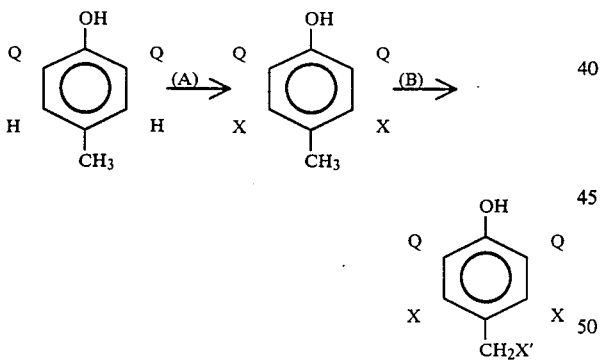

wherein
Q, X and X' are as defined herein;
the 4-methyl(substituted)phenol of the step (A) is contacted with the halogenating agent, preferably the HALOgenating agent, liberating corresponding hydrogen halide; and
the 4-methyl(substituted)phenol of the step (B) is contacted with the HALOgenating agent, liberating corresponding hydrogen halide.

The 4-methyl(substituted)phenol prepared in the step (A) can be isolated, if desired, purified and even reacted later in time. The step (B) alone is, of course, within the scope of the invention (with Q' of the 4-methyl(substituted)phenol of the formula (II) being X). Preferably, the process is carried out in the same reaction vessel by carrying out both of the steps (A) and (B) without special isolation of any halogenated intermediate 4-methyl(substituted)phenol and generally without intermission of a significant time between the steps (A) and (B).

SPECIFIC EMBODIMENTS

The following examples further illustrate the invention. Parts and percentages are by weight unless specified otherwise.

EXAMPLE 1

Preparation of
4-Bromomethyl-3,5-dibromo-2,6-dimethylphenol
(Tribromomesitol)

A 136.2-g portion of 2,4,6-trimethylphenol (1.0 mole) (93 percent pure; General Electric) is dissolved in 2.0 liters of carbon tetrachloride. Using a water bath for cooling, 205 ml of bromine (4.0 moles) is added at 20° C.–26° C. over a period of 15 minutes. Hydrogen bromide gas is given off during the bromine addition, and a slurry of 3,5-dibromo-2,4,6-trimethylphenol is obtained.

The temperature is increased to 70° C.–75° C., and a solution is obtained. The solution is held at 70° C.–75° C. for 3 hours. The unreacted bromine is removed by distillation with the aid of 1 liter of carbon tetrachloride. When 1 liter of solvent remains with the product, the solution is cooled to 25° C. The light brown solid which is obtained is filtered and is dried under vacuum for 5 hours. A yield of 250 g (67 percent) is obtained, which analysis by gas chromatography shows to be 97 percent tribromomesitol and 3 percent dibromomesitol. The product has a melting point of 144° C.–146° C. and has the following proton nuclear magnetic resonance spectrum (CDCl$_3$), δ: 2.30 (s, 6H), 4.90 (s, 2H), which is consistent with the structure of the product.

EXAMPLE 2

Process Variations: Amount of HALOgenating Agent; Time

A 230-ml portion of bromine (4.5 moles) is added to 1.0 mole of 2,4,6-trimethylphenol (93 percent pure; General Electric) in 2 liters of carbon tetrachloride; the refluxing period is 2 hours, and 260 g of product is obtained (70 percent conversion), otherwise following the work-up of Example 1. The crude solid is analyzed as 99 percent tribromomesitol.

EXAMPLE 3

Process Variations: Aprotic Organic Diluents; Temperatures

A 13.6-g portion of 2,4,6-trimethylphenol (0.1 mole) (99 percent pure; Aldrich Chemical Co.) is dissolved in 200 ml of the following aprotic organic diluent (Diluent), and 20.5 ml of bromine (0.4 moles) is added at 19° C.–23° C. using a water bath for cooling. A solid forms which is slurried, and the slurry is heated at the following reflux temperature (Temp) for 2 hours. The excess bromine is then removed by distillation with the aid of 500 ml additional of the listed aprotic organic diluent, and the remaining diluent is removed under vacuum. The product is weighed and is analyzed by gas chromatography for the conversion and selectivity of the product to 4-bromomethyl-3,5-dibromo-2,6-dimethylphenol, and the yield is calculated. The following is observed.

| Run | Diluent | °C. Temp | grams of Conversion | % Selectivity | % Yield |
|---|---|---|---|---|---|
| A | cyclo-hexane | 76–78 | 34.0 | 63 | 63 |
| B | $CH_2Cl_2$ | 38–39 | 32.9 | 33 | 33 |
| C | $CHCl_3$ | 59–60 | 35.5 | 61 | 61 |
| D | $CCl_4$ | 71–74 | 37.2 | 83 | 83 |
| E | $(CH_2Cl)_2$ | 79–81 | 38.7 | 98 | 98 |
| F | $CH_2BrCl$ | 66–68 | 37.3 | 91 | 91 |

EXAMPLE 4

Pilot Scale Production

Two batches of high purity 4-bromomethyl-3,5-dibromo-2,6-dimethylphenol are efficiently prepared in a 100-gallon (376-liter) Pfaudler glass-lined reactor by the following procedures A and B. Of these, the procedure of Run B is preferred.

A. Preparation

To start, 800 pounds (360 kg) of bromochloromethane is pumped into the reactor for each run. Next, 90° C. (melted) mesitol is vacuum loaded, 84.5 pounds (38.3 kg) in Run A and 113 pounds (51.3 kg) in Run B. Bromine, 347.5 pounds (157.6 kg) in Run A and 437 pounds (198 kg) in Run B, is steadily added over a period of time, 1 hour and 48 minutes in Run A and 2 hours and 8 minutes in Run B, with the reactor stirrer at 125–130 rotations per minute (rpm). Each procedure starts out at 30° C. and is somewhat above 60° C. upon completion of the bromine addition. During each bromine addition, heat is applied to offset the cold (5° C.–10° C.) reflux. Approximately ⅔ of the way through each bromine addition, the temperature is 50° C., and the batch briefly thickens, and the air motor stirrer of the reactor drops 6 rpm in Run A and 12 rpm in Run B. From this point on, the reaction slows considerably.

The cook upon completion of each bromine addition lasts a period of time, 7½ hours in Run A and 8⅓ hours in Run B. Each cook starts at about 68° C., and the temperature upon completion of each cook is about 73° C., and each batch is heated to keep the temperatures generally within this range, and maximum applied heating is carried out while keeping the reactor pressure less than 2 psig (a gauge pressure of less than about 26 kPa) and condenser reflux less than 10° C. by setting the water jacket temperature of the reflux condenser to 3° C.

Upon completion of each reaction, the reactor jacket is set at 60° C. and propylene is sparged in, 9 pounds (4 kg) in Run A and about 4½ pounds (2 kg) in Run B. Neutralization completion is indicated by loss of exotherm temperature and sudden disappearance of colored bromine vapors in the reactor headspace.

Upon completion of the neutralization, each product mixture is allowed to cool slowly, no faster than 20° C. per hour. Product precipitation occurs at about 28° C.–30° C. in Run A and about 35° C. in Run B. Each batch is cooled to 2° C.–4° C. and is dropped into a large batch filter and is next manually transferred to a 20-inch (about 50.8 cm) centrifuge, whereupon completion of centrifugation, solvent remains, 13 percent in Run A and 21.7 percent in Run B. A tan product results, 113 pounds (51.3 kg) in Run A (49 percent yield) and 182 pounds (82.6 kg) in Run B (59 percent yield).

B. Recrystallization

The centrifuged product of Runs A and B are combined, and in a clean 100-gallon Pfaudler reactor, 278 pounds (126 kg) of dry solids from uniformly mixing Runs A and B is slurried in 75 gallons (280 liters) of methylene chloride. The mixture is heated to 60° C. The pressure is 15 psig (a gauge pressure of about 103 kPa). Dissolution occurs near 50° C., and the stirring is maintained at 100 rpm during the heating. The solution is cooled at 20° C. per hour. Crystallization occurs at 44° C., whereupon the stirrer is slowed to 60 rpm. Upon cooling to 20° C., refrigeration is applied to the reactor overnight. The slurry is centrifuged at −3° C. (minus 3° C.) and is dried under vacuum in a 2-foot (61-cm) rotary cone Pfaudler dryer in 3 loads. The product is 212 pounds (96.2 kg) of a white, fluffy solid (76 percent recrystallization yield) which melts at 146° C.–147° C. and is analyzed by gas chromatography to be more than 99 percent pure 4-bromomethyl-3,5-dibromo-2,6-dimethylphenol.

I claim:

1. A 4-HALOmethyl-3,5-dihalo-2,6-disubstituted phenol which is represented by the formula

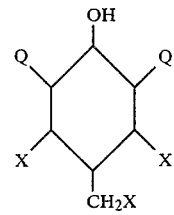

wherein
Q is separately at each occurrence in each formula
$C_{1-12}$ alkyl with the carbon bonded directly to the phenol ring selected from the group consisting of primary and secondary carbons, or
$C_{1-12}$ generally inertly-substituted alkyl;
Q' is hydrogen, fluoro, chloro or bromo; provided that at least one Q' is hydrogen, and
X is separately at each occurrence fluoro, chloro or bromo.

2. The phenol of claim 1 wherein each X is separately chloro or bromo and each Q is separately $C_{1-12}$ alkyl.

3. The phenol of claim 2 wherein each X is bromo and each Q is methyl.

4. The phenol of claim 2 wherein each X is chloro and each Q is methyl.

5. The phenol of claim 2 wherein at least one X is chloro and each one Q is methyl.

* * * * *